United States Patent [19]

Jansons et al.

[11] Patent Number: 4,843,179
[45] Date of Patent: Jun. 27, 1989

[54] PREPARATION OF 4,4'-DIPHENOXYBENZOPHENONE

[75] Inventors: Viktors Jansons, Los Gatos; Heinrich C. Gors, Mountain View, both of Calif.

[73] Assignee: Raychem Corporation, Menlo Park, Calif.

[21] Appl. No.: 141,017

[22] Filed: Jan. 5, 1988

[51] Int. Cl.$^4$ .............................. C07C 45/46
[52] U.S. Cl. ............................. 568/322; 568/319
[58] Field of Search ............... 568/319, 322, 323; 260/544 K

[56] References Cited

U.S. PATENT DOCUMENTS

| | | | |
|---|---|---|---|
| 1,511,646 | 10/1924 | Weaver | 260/544 K |
| 3,138,626 | 6/1964 | Calfee et al. | 562/428 |
| 3,366,691 | 1/1968 | Keller | 568/319 |
| 3,956,240 | 5/1976 | Dahl et al. | 528/220 |
| 4,396,755 | 8/1983 | Rose | 528/220 |
| 4,398,020 | 8/1983 | Rose | 528/207 |
| 4,709,007 | 11/1987 | Jansons et al. | 528/222 |

OTHER PUBLICATIONS

Chem. Abs. 23:5195 (abstract of I. G. Farbenind, GB 307,223, 1928).
Chem. Abs. 62:7672c (abstract of Fumasoni et al., Ann. Chim., Rome, 54,1122, 1964).
Chem. Abs. 77:74905k (abstract of Lebedev et al., Izv. Akad. Nauk. SSS Ser. Khim. 1972, 967).
Chem. Abs. 26:5308 (abstract of Morgan et al., GB 353,464, 1930).

*Primary Examiner*—James H. Reamer
*Attorney, Agent, or Firm*—Yuan Chao; Edith A. Rice; Herbert G. Burkard

[57] ABSTRACT

A method of preparing 4,4'-diphenoxybenzophenone, comprising reacting diphenyl ether and carbon dioxide in the presence of a Friedel-Crafts catalyst and a promoting agent, preferably selected from the group consisting of phosphoryl chloride, phosphorus pentoxide, tetrachlorosilane, methyltrichlorosilane, dimethyldichlorosilane, titanium tetrachloride, zirconium tetrachloride, zirconium oxyhalide, and phosphorus pentachloride. In a preferred embodiment, the Friedel-Crafts catalyst is aluminum chloride and the promoting agent is phosphoryl chloride.

6 Claims, No Drawings

PREPARATION OF 4,4'-DIPHENOXYBENZOPHENONE

BACKGROUND OF THE INVENTION

This invention relates to a method of preparing 4,4'-diphenoxybenzophenone.

4,4'-Diphenoxybenzophenone (DPBP) is useful inter alia as a monomer in the preparation of poly(arylene ether ketones) by Friedel-Crafts polymerization. See, e.g., the disclosures of Dahl et al., in U.S. Pat. No. 3,956,240; Rose, in U.S. Pat. No. 4,396,755 and U.S. Pat. No. 4,398,020; and Jansons et al., in U.S. Pat. No. 4,709,007.

Keller, in U.S. Pat. No. 3,366,691, proposed to make DPBP from diphenyl ether and phosgene. However, phosgene is a hazardous material requiring special equipment and handling procedures, making it undesirable as a starting material. Thus, it would be desirable to be able to synthesize DPBP without using phosgene.

We have invented a method of preparing DPBP with carbon dioxide as a starting material.

SUMMARY OF THE INVENTION

This invention provides a method of preparing 4,4'-diphenoxybenzophenone, comprising reacting diphenyl ether and carbon dioxide in the presence of a Friedel-Crafts catalyst and a promoting agent, preferably selected from the group consisting of phosphoryl chloride, phosphorus pentoxide, tetrachlorosilane, methyltrichlorosilane, dimethyldichlorosilane, titanium tetrachloride, zirconium tetrachloride, zirconium oxyhalide, and phosphorus pentachloride.

DETAILED DESCRIPTION OF THE INVENTION

The starting materials for the method of this invention are diphenyl ether and carbon dioxide. The carbon dioxide can be added to the reaction mixture in the form of dry ice or as gas from a cylinder. The relative stoichiometry of the two materials is not critical. Large excesses of carbon dioxide, for example even over 10-fold stoichiometric excess, may be charged into the reaction vessel, and in fact may be desirable to increase its dissolution in the reaction mixture. Preferably, the molar ratio of carbon dioxide dissolved in the reaction mixture to diphenyl ether is between about 1:2 and about 100:1, but a large excess of gaseous (or undissolved) carbon dioxide generally is needed to cause the concentration of dissolved carbon dioxide to approximate these values. Conversely, the stoichiometry of dissolved carbon dioxide to diphenyl ether may be lower than 1:2, provided there is a sufficient reserve of undissolved carbon dioxide in the reaction vessel, which can go into solution as dissolved carbon dioxide is consumed by the reaction.

The reaction is carried out in the presence of a Friedel-Crafts catalyst, suitable examples of which are aluminum trichloride, aluminum tribromide, antimony pentachloride, antimony pentafluoride, gallium trichloride, boron trichloride, boron trifluoride, ferric chloride, molybdenum pentachloride, and their mixtures. Aluminum trichloride is preferred.

The reaction is further carried out in the presence of a promoting agent, by which is meant an agent capable of converting a carboxylic acid or its salts to a Friedel-Crafts reactive derivative such as an anhydride or acid halide, but which agent itself does not enter into Friedel-Crafts type reactions. Preferably, the promoting agent is selected from the group consisting of phosphoryl chloride, phosphorus pentoxide, tetrachlorosilane, methyltrichlorosilane, dimethyldichlorosilane, titanium tetrachloride, zirconium tetrachloride, zirconium oxyhalide, and phosphorus pentachloride. More preferably, it is selected from the group consisting of phosphoryl chloride, tetrachlorosilane, phosphorus pentachloride, and phosphorus pentoxide. Phosphoryl chloride (also known as phosphorus oxychloride) is most preferred.

The amount of promoting agent should be at least about 1 equivalent per 2 moles of diphenyl ether. The molar amount of Friedel-Crafts catalyst is preferably at least about equal to the total molar amount of promoting present, if the promoting agent is a basic, for example an oxygenated species such as phosphorus oxychloride, plus one-half of the molar amount of diphenyl ether.

While we do not wish to be bound by any theory, it is our belief that the promoting agent promotes the conversion of the intermediate 4-phenoxybenzoic acid (or its salt or complex) to the corresponding acid chloride, anhydride, or other Friedel-Crafts reactive intermediate, enabling further conversion to the ketone. Thus, where diphenyl ether and carbon dioxide are reacted in the presence of a Friedel-Crafts catalyst but in the absence of a promoting agent, some 4-phenoxybenzoic is obtained, but little if any DPBP.

It is another unexpected feature of this invention that the reaction yields little or no polymer attributable to the polymerization of the intermediate 4-phenoxybenzoic acid or its acid chloride. In the absence of a promoting agent, the increasingly severe conditions required to effect conversion of the intermediate 4-phenoxybenzoic acid (or its salt or complex) to DPBP leads to the formation of undesirable oligomeric or polymeric products.

The reaction is conveniently carried out in a pressurized reactor at a temperature between about 70 and about 200° C., preferably between about 130° and about 160° C., depending on the time of reaction, and at a pressure of between about atmospheric and about 1500 psi, preferably between about 300 and about 1000 psi.

EXAMPLE 1

An 100 mL pressure reactor (Parr Instruments Co.), equipped with a magnetically coupled stirrer and a thermocouple, was charged with diphenyl ether (12.00 g, 70.48 mmol, Eastman Kodak) and phosphoryl chloride (5.42 g, 35.45 mmol, Aldrich). The total amount of basic species (diphenyl ether plus phosphoryl chloride) was 105.93 mmol. The mixture was stirred at room temperature, unpressurized and under nitrogen, until the diphenyl ether was dissolved. Aluminum trichloride (14.16 g, 106.2 mmol, Witco 0098) was then added. An exotherm ensued and an easily stirrable slurry resulted. Carbon dioxide (10.7 g, 243 mmol), in the form of a shaved chunk of dry ice (weighed in a sealed polyethylene bag), was added. The reactor was sealed.

The reactor was heated for 1¼ hr at 148° C., followed by 2 hr at 148°-154° C., during which latter period the internal pressure reached 850–900 psi. Upon cooling to room temperature, there was a residual pressure of 515 psi. The reaction mixture appeared to have thickened.

The reactor was slowly degassed, during which process the viscosity of the reaction mixture increased until it could no longer be stirred. Upon opening the reactor, an orange, taffy-like highly viscous mass was found. This was worked up by pouring into water (ca. 500 mL), yielding a granular pink precipitate. The precipitate was washed with more water, digested in refluxing methanol (500 mL), and collected by filtration after cooling. The filter cake was washed with more methanol and then dried in vacuo at 100° C. (The methanol filtrate was stripped to dryness, yielding a crystalline residue (2.03 g) consisting predominantly of a mixture of diphenyl ether and DPBP, with no indication of any p-phenoxybenzoic acid being present.)

Crude DPBP (9.13 g, 70.7% yield based on diphenyl ether) was pinkish and had mp 142°–145° C. Its IR spectrum matched that of an authentic sample. DPBP recrystallized from tetrachloroethylene (63.7 % yield) had mp 145°–147° C. (Keller, cited supra, reports mp 146°–147° C.)

EXAMPLE 2

An 100 mL pressure reactor (Parr Instruments Co.), equipped with a magnetically coupled stirrer and a thermocouple, was charged with diphenyl ether (12.00 g, 70.48 mmol, Eastman Kodak) and phosphoryl chloride (5.42 g, 35.45 mmol, Aldrich). The total amount of basic species (diphenyl ether plus phosphoryl chloride) was 105.93 mmol. The mixture was stirred at room temperature, unpressurized and under nitrogen, until the diphenyl ether was dissolved. Aluminum trichloride (14.10 g, 105.27 mmol, Witco 0098) was then added. An exotherm ensued and an easily stirrable slurry resulted. The reactor was sealed and 610 psig of carbon dioxide gas was applied.

The reactor was heated for 1¼ hr at 148° C., followed by 3 hr at 153°–157° C., during which latter period the internal pressure reached 940–960 psig. Upon cooling to room temperature, there was a residual pressure of 550 psig. The reaction mixture appeared to have thickened.

The reactor was slowly degassed, during which process the viscosity of the reaction mixture increased until it could no longer be stirred. Upon opening the reactor, an orange, foamy, semi-brittle mass was found. This was worked up by pouring into water (ca. 400 mL), yielding a granular pink precipitate. The precipitate was boiled with water, then refluxing methanol (500 mL), and collected by filtration after cooling. The filter cake was washed with more methanol and then dried in vacuo at 90° C. (The combined methanol filtrates were stripped to dryness, yielding a crystalline residue (1.71 g) consisting predominantly of a mixture of diphenyl ether and DPBP, with no indication by TLC of any p-phenoxybenzoic acid being present.)

The crude, light pink DPBP (10.2 g, 79% yield based on diphenyl ether) had mp 142°–145° C. Its IR spectrum matched that of an authentic sample. After recrystallization from methyl ethyl ketone (and treatment with alumina and decolorizing charcoal) afforded purified DPBP (9.68 g, 75 % yield), mp 145°–147° C.

EXAMPLE 3

In this comparative example not according to our invention, diphenyl ether and carbon dioxide are reacted in presence of aluminum chloride, but in the absence of a promoting agent.

A stirrer-equipped, glass-lined autoclave was charged with diphenyl ether (170.21 g, 1.00 mole), aluminum chloride (133.35 g, 1.00 mole), and carbon dioxide (as dry ice, 91.00 g, 2.07 mole). The autoclave was closed and the reactants were gradually heated over about 35 min. to a temperature of 80° C., at which time the pressure was 405 psi. The contents were retained at a temperature between 90° and 100° C. for another 17 hrs. During this time the pressure ranged between 378 and 405 psi. Thin layer chromatography showed the presence of three materials.

After cooling, ice water was added to the dark yellow, crystalline reaction mass. After filtration, the solid filter residue was digested with aqueous sodium hydroxide over a steam bath. The sodium hydroxide solution was filtered off, and, after washing and drying, the solid residue was identified as diphenyl ether (149 g). The sodium hydroxide solution was neutralized with hydrochloric acid, causing a white precipitate to form. This was extracted with chloroform. Separation of the chloroform layer and taking it to dryness yielded a material (5.6 g) identified as p-phenoxybenzoic acid. No DPBP was isolated.

We claim:

1. A method of preparing 4,4'-diphenoxybenzophenone, comprising reacting diphenyl ether and carbon dioxide in the presence of a Friedel-Crafts catalyst selected from the group consisting of aluminum trichloride, aluminum tribromide, antimony trichloride, gallium trichloride, boron trichloride, boron trifluoride ferric chloride, molybdenum pentachloride, and mixtures thereof and a promoting agent selected from the group consisting of phosphoryl chloride, phosphorus pentoxide, tetrachlorosilane, methyltrichlorosilane, dimethyldichlorosilane, titanium tetrachloride, zirconium tetrachloride, zirconium oxyhalide, and phosphorus pentachloride.

2. A method according to claim 1, wherein the promoting agent is selected from the group consisting of phosphoryl chloride, tetrachlorosilane, phosphorus pentachloride, and phosphorus pentoxide.

3. A method according to claim 1, wherein the promoting agent is phosphoryl chloride.

4. A method according to claim 1, wherein the Friedel-Crafts catalyst is aluminum trichloride.

5. A method according to claim 1, wherein the Friedel-Crafts catalyst is aluminum trichloride and the promoting agent is selected from the group consisting of phosphoryl chloride, tetrachlorosilane, phosphorus pentachloride, and phosphorus pentoxide.

6. A method according to claim 1, wherein the Friedel-Crafts catalyst is aluminum trichloride and the promoting agent is phosphoryl chloride.

* * * * *